United States Patent [19]

Hishinuma et al.

[11] Patent Number: 5,128,268
[45] Date of Patent: Jul. 7, 1992

[54] HALOGEN/CHARGE-TRANSFER COMPLEX GAS MONITOR

[75] Inventors: Masakazu Hishinuma, Yokohama, Japan; Yukio Yanagisawa, Wayland, Mass.

[73] Assignee: President and Fellows of Harvard College, Cambridge, Mass.

[21] Appl. No.: 368,601

[22] Filed: Jun. 20, 1989

[51] Int. Cl.⁵ .................. G01N 27/12; G01N 31/22
[52] U.S. Cl. .................. 436/116; 422/56; 422/57; 422/58; 422/82.01; 422/82.02; 422/82.03; 436/122; 436/133; 436/134; 436/135; 436/168; 436/902
[58] Field of Search ...................... 422/56–58, 422/82.01, 82.02, 82.03; 436/116, 122, 133, 134, 135, 902, 167, 168

[56] References Cited

U.S. PATENT DOCUMENTS 3,888,754  6/1975  Tiefenau .................. 204/195 R
3,909,204  9/1975  Allen .................. 23/254 E
4,267,023  5/1981  Frant et al. .................. 204/1 T

FOREIGN PATENT DOCUMENTS 126109    6/1977  Fed. Rep. of Germany .
48058892  of 0000 Japan .
862901    9/1981  U.S.S.R. .
902708    2/1982  U.S.S.R. .

OTHER PUBLICATIONS

Palmes et al. Am. Ind. Hyg. Assoc. J. 37:570–577, 1976.
Yanagisawa et al. Environment International 8:235–242, 1982.
Suzuki et al., Taiki Osen Gakkaishi 18:544, 1983 (English Abstract from Chem. Abstracts).
Yamamoto et al., J. Electroanal. Chem. 194:197–209, 1985.

Primary Examiner—Jill A. Johnston

[57] ABSTRACT

An apparatus for detecting or measuring the concentration of an analyte gas in a gas sample, which apparatus comprises a donor polymer and a halogen-containing compound positioned to contact the analyte gas and capable of reacting with the analyte gas to yield halogen; and a method for using the apparatus.

21 Claims, 5 Drawing Sheets

HALOGEN/CHARGE-TRANSFER COMPLEX GAS MONITOR

BACKGROUND OF THE INVENTION

This invention relates to gas monitors.

Investigation of the levels of various pollutants in ambient air requires a reliable means of sampling the air and quantitatively determining the presence or concentration of the pollutant of interest. One method of sampling involves continuous monitoring of flowing gases: for example, in one such monitor, carbon monoxide (CO) concentration in stack gases is determined by passing the stack gases over a bed of $I_2O_5$, liberating $I_2$ into the gas stream which is then passed directly over the platinum cathode of a galvanic cell having a halide electrolyte; the concentration of CO is determined from the current generated by the presence of $I_2$ in the electrolyte (U.S. Pat. No. 3,909,204). Another monitor, used for determining ozone concentration in flowing gases, involves direction of the gas flow into a galvanic cell having a potassium iodide (KI)-containing electrolyte; the reaction of ozone and KI is according to the following expression:

$$2KI + O_3 \rightarrow K_2O + O_2 + I_2$$

yielding free iodine ($I_2$) that can be determined by applying a voltage across the cell and measuring the resulting current (U.S. Pat. No, 3,888,754).

Another sampling method pumps a known volume of air into a detection device capable of measuring the amount of a given analyte gas in that sample. Still another widely-used sampling technique relies upon molecular diffusion of gases: this passive type of sampler has proven to be comparatively simple, lightweight, easy to use, inexpensive and nonhazardous, and therefore more suitable for certain applications. Multiple passive gas monitors can be used to make simultaneous multi-point measurements or repeated measurements over time at a single location, and are therefore an important tool for large-scale air pollution studies involving wide temporal or spatial variables. Also, the passive design may be incorporated into a device intended to monitor an individual's personal exposure to a given pollutant over a period of time.

Generally, the passive gas sampler consists of a collection apparatus containing a collecting medium. The apparatus is typically a container with an orifice at one end to permit ambient gases to diffuse in and thereby contact the collecting medium.

The collecting medium may take various forms. Some trap molecules of pollutant gas by adsorption, later releasing the gas upon heating, reduction of atmospheric pressure, or treatment with a solvent. For example, benzene vapor may be adsorbed to an activated charcoal collecting medium for subsequent release and analysis. In another type of monitor, the collecting medium may be a reagent that traps the pollutant gas by chemically reacting with it; one example is triethanolamine, a liquid reagent used to collect $NO_2$ (e.g., Palmes et al., Am. Ind. Hyg. Ass. J. 37:570-577, 1976; Yanagisawa et al., Environ. Int. 8:235-242, 1982). Suzuki et al (Taiki Osen Gakkaishi 18:544. 1983) describe a passive monitor for measuring the concentration of oxidant gases that utilizes a filter paper impregnated with 10% neutral-buffered KI aqueous solution. Exposure of the monitor to oxidant gases causes KI on the filter paper to undergo a reaction, liberating $I_2$ which is extracted from the filter paper and titrated with a sodium thiosulfate solution to determine the amount of $I_2$ present, a measure of the amount of ozone or other oxidant gas to which the monitor has been exposed. The accuracy of this technique depends in part upon the degree of sublimation of liberated $I_2$ during exposure, storage and analysis of the monitor. Another type of passive gas monitor is described by U.S Pat. No. 4,267,023, wherein gases diffuse into an electrolyte solution held in a wearable container. A measurable chemical reaction occurs between certain gas species and a constituent of the electrolyte (e.g., $SO_2$ gas will react with $HgBr_2$ in the electrolyte to form Br ions, which can be quantified in an electrochemical cell.

SUMMARY OF THE INVENTION

In general, the invention features a device for detecting or measuring the concentration of an analyte gas (defined as a gas capable of reacting with a halogen-containing compound to form free (molecular) halogen) in a gas sample, which device comprises a donor polymer (defined as a substance capable of forming a charge-transfer complex with a halogen molecule) and a halogen-containing compound capable of reacting with the analyte gas to yield halogen, such halogen-containing compound being positioned to contact the analyte gas.

In preferred embodiments,

1. The analyte gas is ozone (including other ambient oxidant gases which may be present in the gas sample), $NO_2$, $SO_2$, $CO_2$ or CO; more preferably the analyte is a gas or combination of gases that is capable of liberating molecular halogen (e.g. $I_2$) from a halide (e.g. iodide) compound, for example by oxidation of the halide.

2. The donor polymer is nylon-6, poly(2-vinylpyridine), poly(4-vinylpyridine), poly(ethylene oxide), poly(tetrahydrofuran), polyvinyl alcohol, poly(acrylonitrile), poly(N-vinylpyrrolidone), or poly (methyl methacrylate), and more preferably is nylon-6;

3. The halogen-containing compound is an iodine compound, e.g., KI, $I_2O_5$, $KIO_3$ or $CaI_2$, more preferably KI;

4. The device is adapted to be worn by an individual, or alternatively, to be a stationary monitor; and 5. The apparatus includes a means of substantially removing interfering gases (that is, gases, other than the analyte gas, which could react with the halogen-containing compound and the donor polymer on the device to form a charge-transfer complex which, under the measuring procedure employed, interferes with measurement of the charge-transfer complex formed by the analyte gas) from the gas sample before such interfering gases can contact the halogen-containing compound.

The invention also features a method of using the gas sampling device for analysis of the concentration of an analyte gas in a gas sample, by exposing the device to the gas sample for a known period of time and measuring the amount of analyte gas to which the device has been exposed, preferably by measuring the amount of charge-transfer complex on the device, for example by measuring the amount of charge needed in order to reduce electrochemically the entire amount of charge-transfer complex, e.g., by placing it in a discharge cell, reducing the charge-transfer complex at a predetermined current, and measuring the reduction time or "discharge time" (the time elapsed from the start of the reduction current until the charge-transfer complex on the device is reduced to zero volts vs. a Ag/AgCl reference electrode); the concentration of the analyte gas is preferably determined from the discharge time by calculation or, alternatively, by reference to a calibrated standard; and preferably any interfering gases present in the gas sample are substantially removed from the gas sample before they can contact the halogen-containing compound.

The invention also features a method of using two such gas sampling devices for analysis of the concentration of an analyte gas in a gas sample containing one or more interfering gases, one of which devices is equipped with a means for substantially removing the analyte gas from the gas sample before the analyte gas can contact or react with the halogen-containing compound: after exposure of both devices to the gas sample for a period of time, the total amount of charge-transfer complex on each is measured, and the concentration of the analyte gas is determined from the differential.

The apparatus of the invention utilizes the known ability of certain halogen-containing compounds, such as KI, to react with certain reactive gases, such as ozone, to liberate halogen, such as $I_2$. By causing the halogen to form a stable charge-transfer complex with a donor polymer, the invention overcomes the tendency of halogen so produced to sublimate before analysis can be accomplished. In addition to stabilizing the halogen reaction product, formation of this charge-transfer complex also provides a highly convenient means of analyzing the amount of halogen produced, which is a measure of the amount of analyte gas to which the halogen-containing compound was exposed. Measuring discharge time in a discharge cell is a simple, quick and accurate method of analysis that would lend itself to individual readings or wide-scale air pollution studies involving a large number of samplers. The apparatus itself is simple and inexpensive to manufacture, is lightweight and compact enough to be incorporated into a personal monitor, may be stored for at least a week after exposure with no detectable decomposition of the charge-transfer complex, and exhibits superior sensitivity, reproducibility and accuracy.

Other features and advantages of the invention will be apparent from the following description of the preferred embodiments thereof and from the claims.

DESCRIPTION OF THE PREFERRED EMBODIMENTS

The drawings are first described.

DRAWINGS

THE HALOGEN/CHARGE-TRANSFER COMPLEX GAS MONITOR

The design of the halogen/charge-transfer complex gas monitor is based upon the ability of certain gases to react with a halogen-containing compound, forming free halogen. Although the halogen so produced is somewhat volatile, in the presence of a donor polymer such as nylon-6{poly(caprolactam)}, free halogen is absorbed to form a relatively stable charge-transfer complex with the donor polymer, minimizing the loss of halogen from the monitor both during exposure and during storage after exposure. The amount of halogen collected by the monitor can be measured by any of a number of techniques, including releasing the halogen from the charge-transfer complex into a solvent and (1) measuring light absorbance of the resulting solution at an appropriate wavelength of light, or (2) titrating the resulting solution with, for example, a sodium thiosulfate aqueous solution. Preferably, the amount of halogen collected by the monitor is conveniently and accurately determined by measuring the amount of charge-transfer complex accumulated on the monitor. This may be accomplished by utilizing the exposed monitor as the positive electrode of a galvanic cell, and measuring the time it takes to reduce the charge-transfer complex on the monitor, at a predetermined current.

EXAMPLE 1

Preparation of Nylon-6/KI Halogen/Charge-Transfer Complex Gas Monitor

Figure 1A:
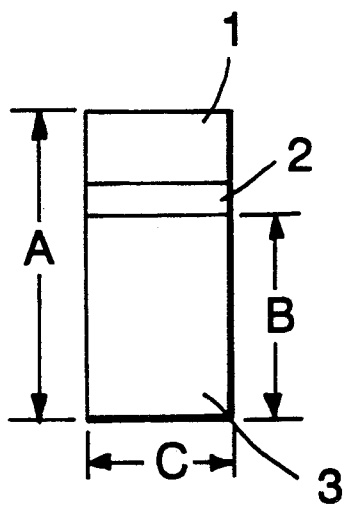
FIG. 1 is a schematic diagram of one embodiment of the halogen/charge-transfer complex gas monitor, shown in a frontal view (a) and a side view (b).
Figure 1B:
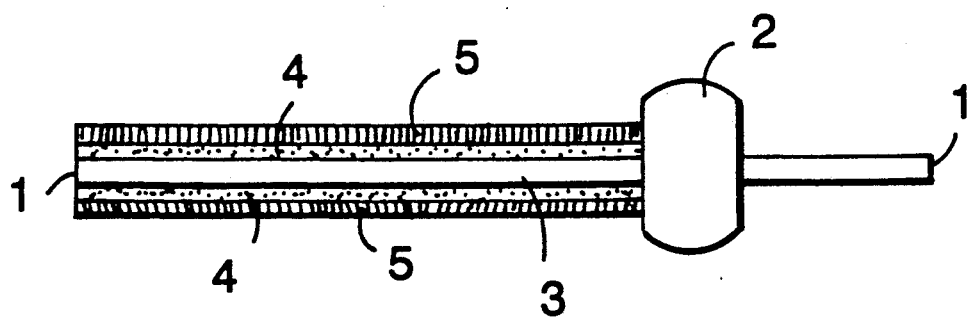

One embodiment of the halogen/charge-transfer complex gas monitor is illustrated in FIG. 1. A carbon fiber plate 1 (Kurehe KCF-100, Japan) was cut to 1.5×3 cm, washed with distilled water and methanol, and dried. A parafilm (American Can Company, Greenwich, CT) diffusion barrier 2 was placed around the plate, near one end, leaving a 1.5×2 cm area 3 uncovered and available for coating with donor polymer 4. Nylon-6 (40 mg, Aldrich Chemical Company, Inc., Milwaukee, WI) was dissolved in 4 ml of purified methanol saturated with $CaCl_2$. Upon dissolution of nylon-6 into the methanol/$CaCl_2$ mixture, 4 ml of methanol and 8 mg of carbon powder (Kehen Black EC, West Germany) were added at room temperature with stirring. The uniformly dispersed mixture was removed by pipette and spread uniformly on both sides of the uncovered 1.5 ×2 cm areas of the carbon fiber plate. The coated plate was dried in a vacuum oven at 60° C. for 2 hr. After drying, the plate was washed in an ultrasonic cleaner bath with methanol and then with distilled water in order to remove $CaCl_2$ from the plate, followed by drying in the vacuum oven at 60° C. for 24 hr. A 0.1 N solution of potassium iodide 5 (Aldrich Chemical Company, Inc. Milwaukee, WI) in a 2:1 mixture of distilled water and methanol was spread by pipette over the donor-polymer-coated section of the carbon fiber plate. Finally, the plate was dried and stored in a vacuum oven controlled at 60° C.

EXAMPLE 2

Experimental Exposure of the Monitor to Gas Samples.

Figure 2:
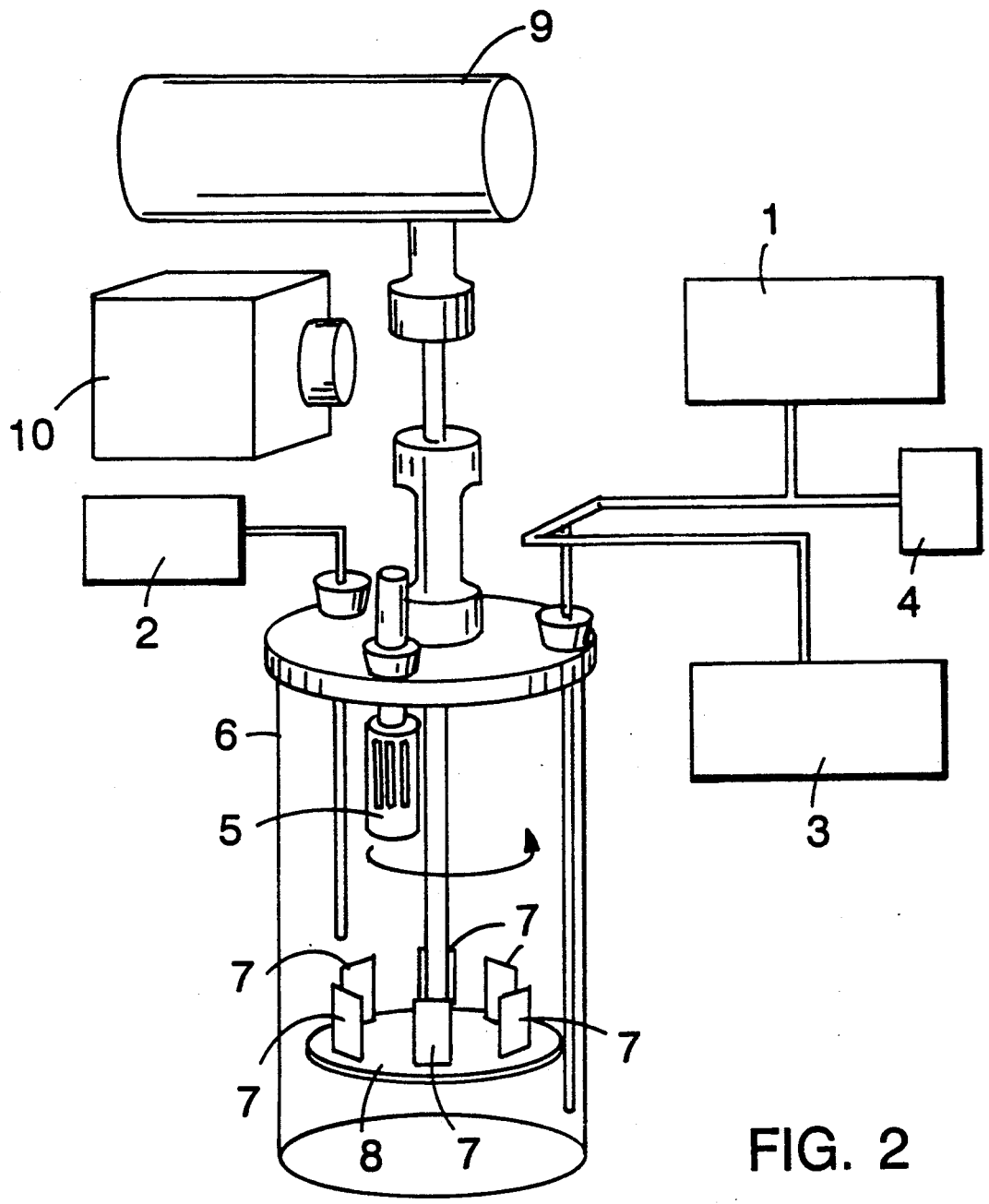
FIG. 2 is a schematic diagram of the apparatus utilized for exposing the halogen/charge-transfer complex gas monitor to gas samples under controlled conditions.

An exposure chamber, illustrated in FIG. 2, was designed to permit testing of the halogen/charge-transfer complex gas monitor at controlled exposure levels. An Ozone Calibrator Mode 49PS 1 (Thermo Electron Corp., Waltham, MA) was used to generate ozone, the concentration of which inside the exposure chamber was continuously monitored by an Ozone Analyzer Model 8410E 2 (Monitor Labs Inc., San Diego, CA). A Dynacalibrator Model 340 3 (Metronics Inc., Santa Clara, CA) was used to generate $NO_2$ (at 66ppb) and $SO_2$ (at 46ppb).

The relative humidity of the gas sample was controlled by means of a humidifier 4 attached to the gas line, and was monitored by means of a humidity sensor 5 (Model HMP 113A, VAISALA, Finland) inside the exposure chamber 6.

The exposure chamber temperature was controlled by placing the chamber in an incubator at 25° C. (Model 815, GCA Corp.).

The halogen/charge-transfer complex gas monitors 7 were mounted upright on a turntable 8 suspended inside the exposure chamber, which turntable was turned at a predetermined rate by a stirring motor 9 monitored by an optical tachometer 10 in order to ensure uniform exposure of all halogen/chargetransfer complex gas monitors in the chamber. Strong UV light (such as sunlight) was avoided, as it could lead to degeneration of the charge-transfer complex.

EXAMPLE 3

Electrochemical Reduction of the Charge-Transfer Complex in a Discharge Cell

Figure 3A:
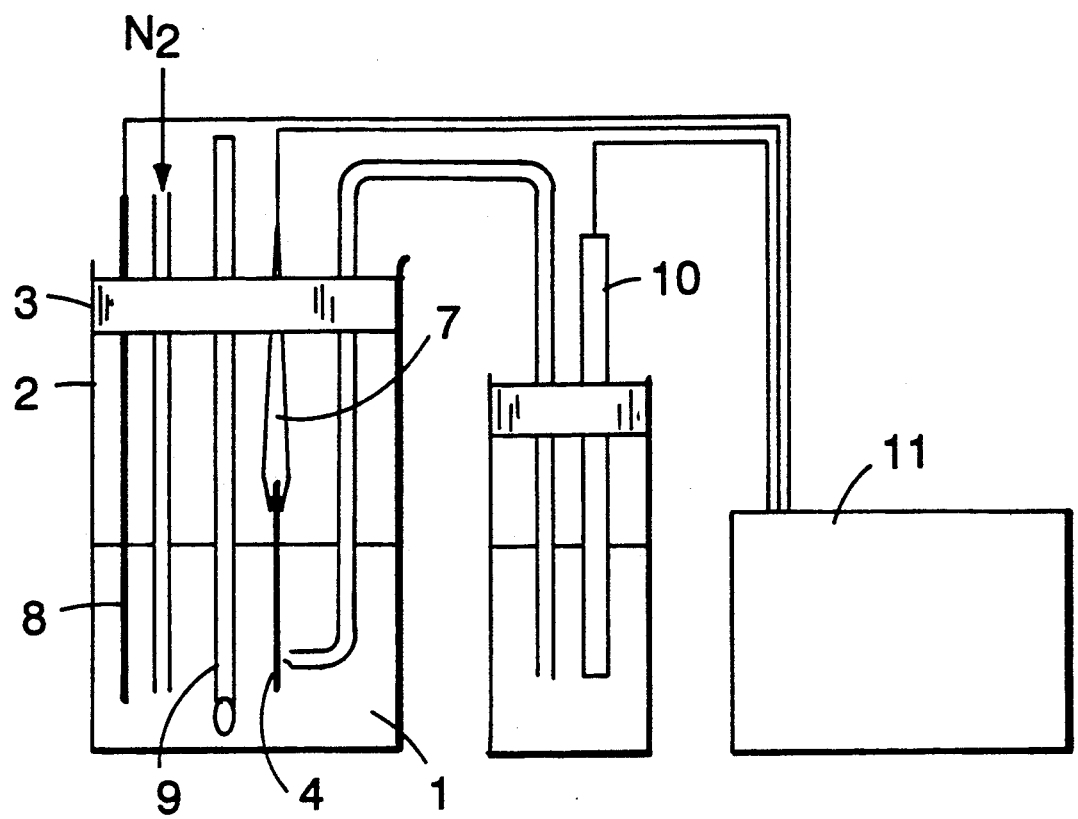
FIG. 3 is a schematic diagram of the discharge cell.
Figure 3B:
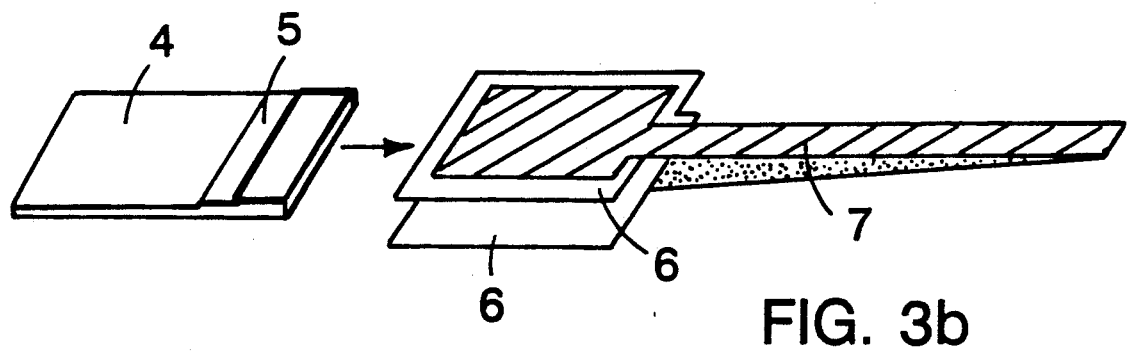

FIG. 3 illustrates the discharge cell used to measure the amount of charge-transfer complex accumulated on each halogen/charge-transfer complex gas monitor during the course of exposure to the sample gas. An electrolyte consisting of 200 ml of 0.1 M $NH_4Cl$ aqueous solution 1 was placed in a beaker 2 (400 ml, Pylex) with a plastic cap 3. The previously exposed halogen/-charge-transfer complex gas monitor 4, immersed in the electrolyte up to the parafilm strip 5, served as the positive electrode. The monitor was clamped between two platinum plates 6 attached to a forceps 7, and was thus held in place in the electrolyte.

Figure 4:
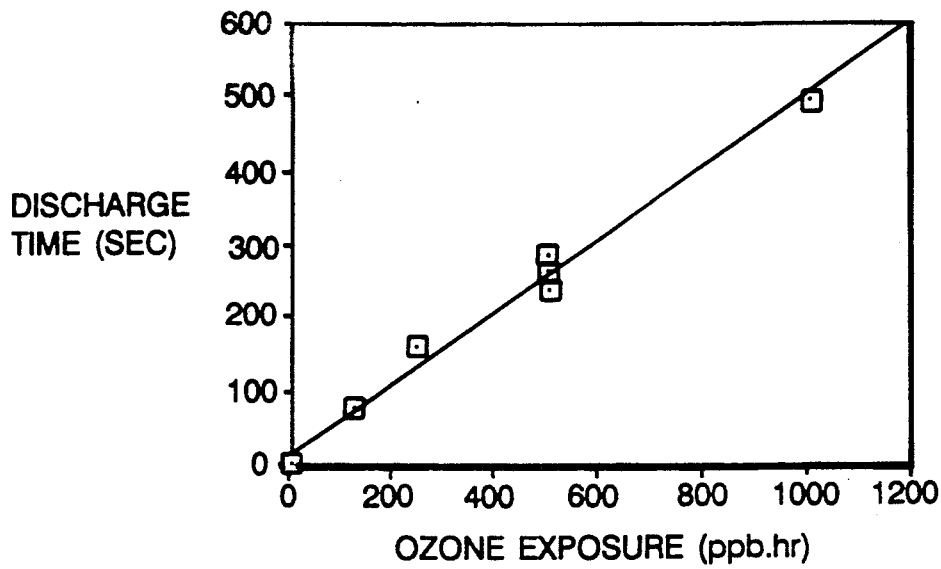
FIG. 4 is a graph of discharge time as a function of ozone exposure.

A zinc plate 8 (ca $5 \times 10$ cm) immersed in the electrolyte served as the negative electrode. Oxygen was purged from the cell by bubbling nitrogen gas into the electrolyte. The discharge cell was placed in an incubator to keep the temperature at 25° C., monitored by a thermometer 9 immersed in the electrolyte. The potential on the positive electrode was monitored versus an Ag/AgCl reference electrode 10 (0.222V vs normal hydrogen electrode). Both electrodes were connected to a potentiostat/galvanostat 11 (Model HA-301, Hokuto, Japan) to maintain the discharge current at 100 $\mu$A throughout the discharge procedure and to monitor the voltage drop during he course of the discharge. Discharge time was the time elapsed from the start of the discharge procedure until the electrical potential on the halogen/chargetransfer complex gas monitor dropped to zero volts vs. a Ag/AgCl reference electrode. FIG. 4 illustrates the linear relationship between ozone exposure (in ppb.hr) and discharge time for a monitor coated with nylon-6 and KI. In order to confirm reproducibility, the ozone exposure and discharge procedure was repeated four times at an exposure of 500 ppb.hr (125 ppb for 4 hr): mean discharge time for the four trials was 263 sec with a coefficient of variance of 6.4% and 95% confidence interval of $263 \pm 27$ sec. Slope, intercept, and coefficient of determination ($r^2$) calculated by a least-square method were 0.49 sec/ppb-hr, 16 sec, and 0.99, respectively. Discharge time obtained from an unexposed monitor was 2 sec.

EXAMPLE 4

Comparing Responses to Ozone, $NO_2$ and $SO_2$ Exposure

Figure 5:
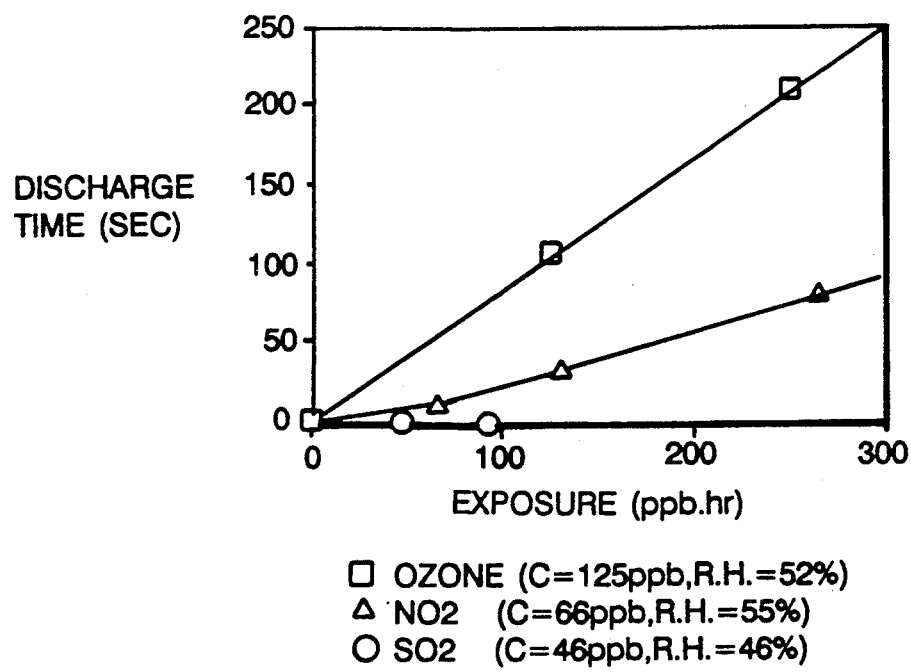
FIG. 5 is a graph of discharge time as a function of exposure to ozone, $NO_2$ or $SO_2$.

Halogen/charge-transfer complex gas monitors coated with nylon-6 and KI were exposed to ozone, $NO_2$ or $SO_2$ and their discharge times for given exposure levels (in ppb.hr) compared. FIG. 5 shows that both ozone and $NO_2$ will develop a charge-transfer complex on the monitor, with a measurable discharge time that increases linearly with exposure to the gas, while $SO_2$ (at exposures up to 92 ppb.hr) apparently does not. The slope of the line for $NO_2$ exposure was lower for exposures less than 66 ppb.hr than for those above 66 ppb.hr, possibly due to adsorption of $NO_2$ by the inner walls of the chamber at the start of the exposure period, which would make the concentration of available $NO_2$ inside the chamber during the first part of the exposure period lower than the concentration indicated by the $NO_2$ generator during that time. The slope of the line for $NO_2$ exposure above 66 ppb.hr was 0.39, with $r^2 = 0.99$.

EXAMPLE 5

Figure 6:
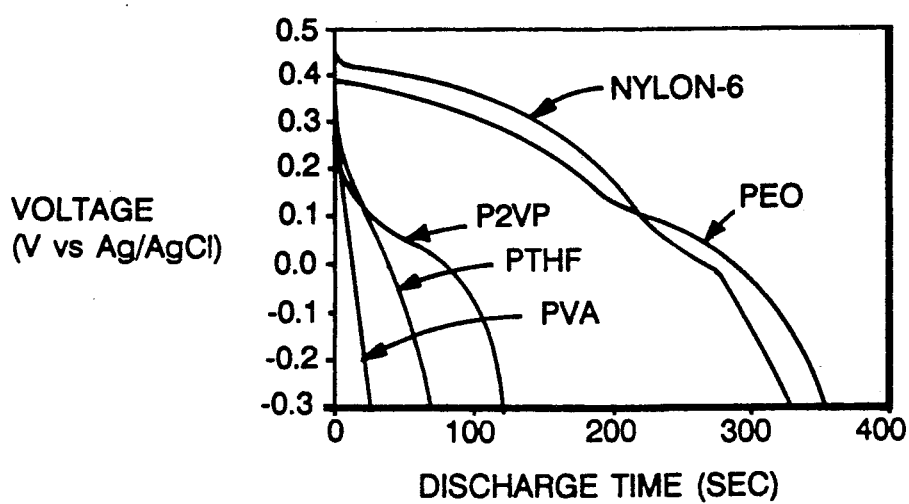
FIG. 6 is a graph of the discharge curves of halogen/charge-transfer complex gas monitors incorporating various donor polymers, where the exposed monitors were discharged immediately following exposure to ozone.
Figure 7:
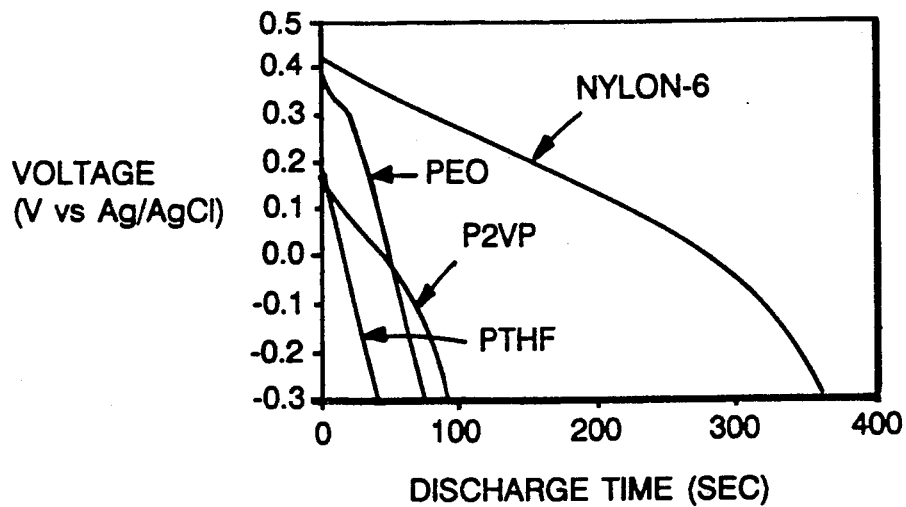
FIG. 7 is a graph of the discharge curves of halogen/charge-transfer complex gas monitors incorporating various donor polymers, where the exposed monitors were stored for a week prior to effecting discharge.

Comparison of Halogen/Charge-Transfer Complex Gas Monitors Employing Various Donor Polymers Monitors coated with donor polymers other than nylon-6 were prepared generally as described in Example 1, except that instead of being dissolved in methanol/$CaCl_2$, the polymers poly(ethylene oxide) (PEO) and poly(vinyl alcohol) (PVA) were dissolved in water; poly(2-vinylpyridine) (P2VP) was dissolved in methanol; and poly(tetrahydrofuran) (PTHF) was dissolved in ethanol. In addition, the ultrasonic cleaner bath washing step utilized for nylon-6 was eliminated for the other donor polymers. A comparison of the performance of each type of donor polymer as a constituent of an halogen/charge-transfer complex gas monitor is shown in FIG. 6 (where discharge was accomplished immediately after exposure at 125 ppb ozone for 4 hr at 25° C.), and FIG. 7 (where, following exposure at 125 ppb ozone for 4 hr at 25° C., the exposed monitors were stored for one week prior to being discharged).

OTHER EMBODIMENTS

Other embodiments are within the following claims. For example, donor polymers other than nylon-6, PEO, P2VP, PTHF and PVA may be employed, and the amount of donor polymer deposited per unit area may be increased or decreased. The amount of carbon powder mixed with the donor polyer may be varied, or other means for increasing the electrical conductivity of the coated monitor may be employed. The size and shape of the carbon fiber substrate may be altered, or a different conductive material (e.g. silver, or a material which can directly form a charge-transfer complex with liberated halogen and thus eliminate the necessity to coat with a donor polymer) may be substituted. The solubilized donor polymer may be mixed with the halogen-containing compound for a single-step coating procedure.

Halogens other than iodine (such as bromine) may be used, or an iodine compound other than KI (such as $I_2O_5$, $KIO_3$ or $CaI_2$) may be substituted, and the amount of the compound deposited on the monitor may be varied. Using the general experimental methods and other information described herein, those skilled in the art will understand how to optimize selection of the halogen-containing compound for a given analyte gas. As noted above, KI or other halide compounds may be used for $NO_2$ or ozone. $I_2O_5$ may be used to measure carbon monoxide concentration $CaI_2$ may be used to measure carbon dioxide concentration, and $KIO_3$ may be used to measure acidic gases such as $NO_2$ and $SO_2$. The analyte gas may be distinguished from interfering gases by incorporating a mechanism to remove interfering gases prior to their reacting with the halogen-containing compound: for example, a diffusion screen mounted in front of the monitor can be coated with a substance (such as a reactant, an adsorbant or a catalyst) that will adsorb or eliminate the interfering gases. A diffusion screen coated with a polydiene could be used to remove ozone, for example, while an alkali-coated screen could remove $NO_2$.

Alternatively, the analyte gas may be measured indirectly by using two monitors, one of which measures the analyte gas as well as an interfering gas, and the other of which has a mechanism to remove the analyte gas, so that the latter measures only the interfering gas; the difference between the two measurements may be attributed to the analyte gas.

The monitor may be coated on only one side instead of both. It may be incorporated into a holder suitable to be worn as a "badge" for monitoring personal exposure to an analyte gas, or it may be adapted to serve as a stationary monitor, e.g. by placing it behind a protective screen in a case which can be set on a horizontal surface or mounted on a wall.

Determination of the concentration of the analyte gas in the gas sample may be accomplished, for example, by calculating the concentration from the discharge time, the exposure period, and other known quantities, or by reference to a calibrated standard, such as a graph or a table.

The monitor could be adapted to be incorporated into an active-sampler gas monitor by, for example, including a pump or flow-deflection mechanism to introduce a measured volume of sample gas into the monitor's exposure chamber.

We claim:

1. An apparatus for analyzing a gas sample comprising an analyte gas, said apparatus comprising,
   a solid surface;
   a donor polymer;
   a halogen-containing compound capable of reacting with said analyte gas to yield free halogen, said halogen-containing compound being in solid form; and
   means for maintaining said halogen-containing compound adjacent to said donor polymer and in fixed relationship with said solid surface, said halogen-containing compound being positioned to contact said analyte gas, and said donor polymer being positioned to absorb halogen released by the reaction of said analyte gas with said halogen-containing compound, whereby said donor polymer forms a stable charge-transfer complex with said halogen.

2. The apparatus of claim 1, wherein said halogen-containing compound is characterized in that it reacts with said analyte gas to yield halogen wherein said analyte gas is taken from the group consisting of ozone, $NO_2$, $SO_2$, $CO_2$ and CO.

3. The apparatus of claim 1, wherein said donor polymer is taken from the group consisting of poly(caprolactam), poly(2-vinylpyridine), poly(4-vinylpyridine), poly(ethylene oxide), poly(tetrahydrofuran), poly(vinyl alcohol), poly(acrylonitrile), poly(N-vinylpyrrolidone), and poly(methyl methacrylate).

4. The apparatus f claim 3, wherein said donor polymer is poly(caprolactam).

5. The apparatus of claim 1, wherein said halogen-containing compound is an iodine compound.

6. The apparatus of claim 5, wherein said iodine compound is taken from the group consisting of KI, $I_2O_5$, $KIO_3$ and $CaI_2$.

7. The method of claim 6, wherein said iodine compound is KI.

8. The apparatus of claim 1, wherein said apparatus comprises a holder suitable to be worn by an individual.

9. The apparatus of claim 1, wherein said apparatus comprises a chamber containing said donor polymer and said halogen-containing compound, said chamber comprising means for fixing said apparatus in a stationary position.

10. The apparatus of claim 1, wherein said apparatus comprises means for exposing said apparatus to an analyte gas by diffusion of said analyte gas.

11. The apparatus of claim 1, wherein said apparatus includes a means of substantially removing interfering gases from said gas sample before said interfering gases can contact said halogen-containing compound.

12. The apparatus of claim 1, wherein said apparatus further comprises means for exposing said apparatus to a measured volume of a gas sample.

13. A method for analyzing the concentration of an analyte gas in a gas sample, said method comprising
    providing the apparatus of claim 1,
    exposing said apparatus to said gas sample for a period to time, and
    measuring the amount of said analyte gas to which said apparatus has been exposed.

14. The method of claim 13, wherein said analyte gas is taken from the group consisting of ozone, $NO_2$, $SO_2$, $CO_2$ and CO.

15. The method of claim 13, wherein said amount of said analyte gas is measured by a method comprising measuring the amount of charge-transfer complex on said exposed apparatus.

16. The method of claim 14, wherein said amount of charge-transfer complex is measured by a method comprising
    placing said exposed apparatus in a discharge cell,
    reducing said charge-transfer complex at a predetermined current, and
    measuring the discharge time.

17. The method of claim 16, wherein said concentration of said analyte gas is determined by calculation from said discharge time.

18. The method of claim 17, wherein said concentration of said analyte gas is determined from said discharge time by reference to a calibrated standard.

19. The method of claim 13, wherein any interfering gases present in said gas sample are substantially removed from said gas sample before said interfering gases can contact said halogen-containing compound.

20. A method of analyzing the concentration of an analyte gas in as gas sample having an interfering gas, said method comprising,
providing two of the apparatuses of claim 1, the first of said apparatuses being identical to the apparatus of claim 1, the second of said apparatuses further comprising a means for substantially removing said analyte gas from said gas sample before said analyte gas can contact said halogen-containing compound;
exposing said first apparatus and said second apparatus to said gas sample for a period of time;
measuring the total amount of said analyte gas and said interfering gas to which said first apparatus has been exposed;
measuring the amount of said interfering gas to which said second apparatus has been exposed; and
determining said concentration from the difference between said measurements.

21. A method for analyzing the concentration of an analyte gas in a gas sample having an interfering gas, said method comprising,
providing the apparatus of claim 1, wherein said apparatus further comprises a means for substantially removing said interfering gas from said gas sample before said interfering gas can contact said halogen-containing compound;
exposing said apparatus to said gas sample for a period of time;
measuring the amount of said analyte gas to which said apparatus has been exposed.

* * * * *

UNITED STATES PATENT AND TRADEMARK OFFICE
CERTIFICATE OF CORRECTION

PATENT NO. : 5,128,268

DATED : July 7, 1992

INVENTOR(S) : Masakazu Hishinuma and Yukio Yanagisawa

It is certified that error appears in the above-identified patent and that said Letters Patent is hereby corrected as shown below:

Col. 1, line 14 please insert:

--This invention was made with government support under Grant No. RR 05446 awarded by the National Institutes of Health. The government has certain rights in the invention.--

Signed and Sealed this

Fourth Day of July, 1995

Attest:

BRUCE LEHMAN

*Attesting Officer*  *Commissioner of Patents and Trademarks*